United States Patent [19]

Lo

[11] Patent Number: 5,529,789

[45] Date of Patent: Jun. 25, 1996

[54] METHOD OF PRODUCING POROUS DELIVERY DEVICES

[75] Inventor: Julian B. Lo, Old Lyme, Conn.

[73] Assignee: Pfizer, Inc., New York, N.Y.

[21] Appl. No.: 374,789

[22] PCT Filed: Nov. 6, 1992

[86] PCT No.: PCT/US92/09321

§ 371 Date: Sep. 15, 1994

§ 102(e) Date: Sep. 15, 1994

[87] PCT Pub. No.: WO93/18757

PCT Pub. Date: Sep. 30, 1993

Related U.S. Application Data

[63] Continuation of Ser. No. 852,702, Mar. 17, 1992, abandoned.

[51] Int. Cl.⁶ .................................................. A61K 9/24
[52] U.S. Cl. ........................... 424/473; 424/464; 424/441; 424/480
[58] Field of Search .................................. 424/441, 473, 424/489, 490, 440

[56] References Cited

U.S. PATENT DOCUMENTS

| | | | |
|---|---|---|---|
| 3,885,026 | 5/1975 | Heinemann et al. | 424/14 |
| 4,134,943 | 1/1979 | Knitsch et al. | 264/28 |
| 4,305,502 | 12/1981 | Gregory et al. | 206/532 |
| 4,371,516 | 2/1983 | Gregory et al. | 424/22 |
| 4,616,047 | 10/1986 | Lafon | 823/105 |
| 4,988,512 | 1/1991 | Azria | 424/422 |
| 5,326,571 | 7/1994 | Wright et al. | 424/473 |
| 5,348,746 | 9/1994 | Dong et al. | 424/473 |
| 5,380,532 | 1/1995 | Delevil et al. | 424/473 |
| 5,417,985 | 5/1995 | Coutel et al. | 424/489 |

FOREIGN PATENT DOCUMENTS

| | | |
|---|---|---|
| 1143801 | 12/1987 | Japan . |
| 9109591 | 7/1991 | WIPO . |

*Primary Examiner*—Thurman K. Page
*Assistant Examiner*—William E. Benston, Jr.
*Attorney, Agent, or Firm*—Peter C. Richardson; Gregg C. Benson; A. Dean Olson

[57] ABSTRACT

An efficient method for making high strength, highly porous, fast dissolving delivery devices. The method comprises mixing a formulation comprising menthol, a water-soluble, menthol-soluble polymer, and an active agent at a temperature such that the menthol is substantially molten. The formulation is disposed in a mold, solidified and the menthol is sublimed from the solidified molded formulation. Preferably, the solidification occurs at a temperature sufficient to provide a substantially amorphous menthol structure.

9 Claims, 1 Drawing Sheet

METHOD OF PRODUCING POROUS DELIVERY DEVICES

This application was filed under 35 U.S.C. §371 based on PCT/US92/09321, which was filed on Nov. 6, 1992 published as WO93/18757, sep. 30, 1993, which is a continuation of U.S. application Ser. No. 07/852,702 which was filed on Mar. 17, 1992 and is now abandoned.

BACKGROUND OF THE INVENTION

This invention relates to methods for making porous delivery devices, particularly pharmaceutical tablets.

Pharmaceutical tablets are often administered orally. A rapid disintegration of the tablet in the mouth without mastication or water facilitates administration to patients in general, and to the very young, the elderly, and to non-human animals, in particular.

One type of oral dosage form which is designed to address the problem of swallowing is known as "chewable tablets". These tablets, however, are not fully satisfactory because they require mastication.

Another type of oral dosage form known as the "effervescent tablet" comprises solid adjuvants of an acid and a base. The reaction between the acid and the base in the presence of water gives off carbon dioxide which "blows apart" the tablet to facilitate its dissolution. One type of effervescent tablet that must dissolve in a glass of water for administration requires that the patient drink the water. Aside from the problem of leaving a small amount of residual active agent in the glass, this dosing method is impractical for very young patients. Another type of effervescent tablet that "bubbles" and then dissolves in the mouth is also objectionable to some patient populations, especially the very young. Both types of effervescent tablets are thus not fully satisfactory.

Yet another type of oral dosage form known as the "enteric tablet" is designed to release the pharmaceutical agent in the upper small intestine. A limitation of enteric tablets is that those that fail to disintegrate rapidly in the intestine could pass the "window of absorption" and result in poor bioavailability.

One type of non-oral dosage form known as the birth control pessaries often takes as long as ten minutes to release the foaming agent. For obvious reasons, it is desirable for this type of dosage form to disintegrate rapidly. Tablets that disintegrate rapidly in an aqueous environment are often formulated with disintegration agents, such as starch, microcrystalline cellulose, carboxymethylcellulose sodium, and sodium starch glycolate, etc. These tablets disintegrate at an unsatisfactory rate for some applications described above.

An increased disintegration rate can be obtained by increasing the porosity (void spaces) of the tablet. Void spaces in the tablet matrix facilitate the permeation of water to rapidly erode the entire tablet. It is therefore desirable to obtain tablets of the highest porosity technically achievable.

U.S. Pat. No. 3,885,026 discloses a process for the production of porous tablets. In this process, a solid volatilizable adjuvant is incorporated in the tablet formulation. The tablet is formed by compression, and the volatilizable adjuvant is removed by sublimation or thermal decomposition. Exemplary volatilizable adjuvants include urethane, urea, ammonium bicarbonate, hexamethylenetetramine, benzoic acid, phthalic anhydride, naphthalene and camphor. The maximum porosity obtained according to this patent is 50% and preferably 10 to 30%. Tablets of high strength at a porosity higher than 50% are difficult to produce by this method.

U.S. Pat. No. 4,134,943 discloses the production of porous tablets by mixing the tablet components with a liquid solvent which is inert towards the tablet components. Suitable solvents include water, cyclohexane, benzene, etc., which freeze at a temperature from about −30° to +25° C. The solvent constitutes about 5 to 80% by weight of the total mixture. The mixture is divided or sprayed into small particles or droplets which are subsequently frozen into solid flowable granules. These granules are pressed into tablets at a temperature below the freezing point of the solvent, and then the solvent is sublimed from the tablets. The porosity of the resultant tablets corresponds to the amount of solvent that is removed from the tablet. The maximum porosity of the tablets produced by this method is 80%. The method of production in this patent is relatively complex since it involves the preparation of frozen granules.

Finally, U.S. Pat. Nos. 4,305,502 and 4,371,516 disclose the production of shaped articles by freezing, in a mold, a water-based pharmaceutical composition, and subliming the water from the frozen composition to form porous articles. Because the articles produced by this process have weak, easily broken meniscuses, U.S. Pat. No. 4,305,502 reduces the amount of handling of the articles by forming them in situ in the depressions of a filmic packaging substrate.

A commercial product based on U.S. Pat. No. 4,305,502 is known as R.P. Scherer's Zydis™. A similar type of porous article known as Quicksolv™ by Mediventure Inc. (International Publication No. WO 91/09591) is made by a solvent exchange process which removes the water from the frozen matrix (instead of by lyophilization). Since both Zydis™ and Quicksolv™ are formed from an aqueous composition, pharmaceutical agents that are sensitive to water (because of stability or taste masking) are not suitable for these systems. In addition to the compatibility problem with aqueous compositions, the frozen matrix tends to stick to the mold in which the aqueous composition is frozen. This is in part due to the fact that water expands upon freezing. To facilitate the release of the product from molds, a surfactant is used in U.S. Pat. Nos. 4,305,502 and 4,371,516.

Although there are a variety of methods for making porous tablets, these methods do not adequately address all the problems. For example, the processes can be complex, the resultant tablets may lack sufficient porosity, the tablets may lack sufficient strength, the composition may be incompatible with the active agents, and the products may stick to the molds. Accordingly, there is a continual search in this art for methods for making highly porous, high strength, fast-dissolving tablets.

SUMMARY OF THE INVENTION

This invention is directed to an efficient method for making high strength, highly porous, fast dissolving delivery devices. The method comprises mixing a formulation comprising menthol, a water-soluble, menthol-soluble polymer, and an active agent at a temperature such that the menthol is substantially molten. The formulation is disposed in a mold, solidified and the menthol is sublimed from the solidified molded formulation. Preferably, the solidification occurs at a temperature sufficient to provide a substantially amorphous menthol structure.

This invention makes a significant advance in the field of delivery devices by providing an efficient method for making non-friable, highly porous devices that disintegrate rapidly in an aqueous medium. The non-porous devices can be easily released from molds and can be handled at ambient conditions prior to pore formation.

Other features and advantages will be apparent from the specification and claims, and from the accompanying drawings which illustrate an embodiment of the invention.

DETAILED DESCRIPTION OF THE INVENTION

Figure 1:
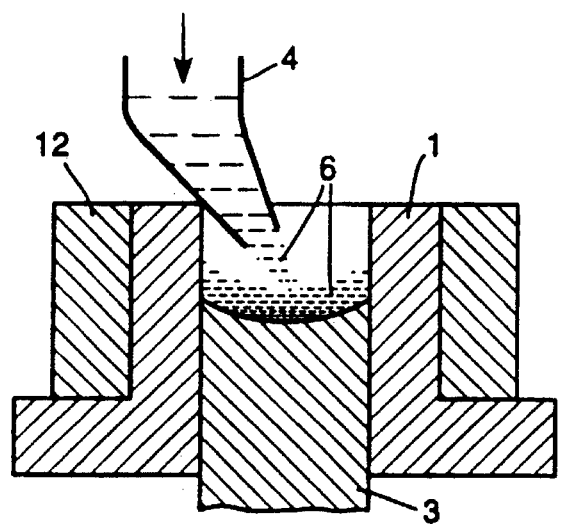
FIG. 1 is a schematic (in cross-section) illustrating the filling of a die with the liquid formulation.

Any low melting point (i.e. M.P. <50° C.) sublimable material may be used as the solvent for the preparation of the formulations of this invention. Preferably a pharmaceutically acceptable solvent such as menthol is used. Typically about 50% to about 99% menthol is used and preferably about 80% to about 95% menthol is used in the initial formulation.

Any water-soluble, menthol-soluble polymer may be employed as the strengthening substance in the devices of this invention. The menthol solubility facilitates the structural strength of the device and the water solubility facilitates the rapid dissolution of the device. The term water-soluble, menthol-soluble polymer is also meant to include lightly cross-linked fine particle polymers, for example, carbomer which is an acrylic acid polymer cross-linked with a polyalkenyl polyether. Preferably, the water-soluble, menthol-soluble polymer is a film-forming polymer. By "film-forming polymers" is meant, as described in "The Theory and Practice of Industrial Pharmacy" by Lachman, Lieberman and Kanig (1970), polymers which are sufficiently soluble in the solvent and are capable of producing a strong continuous film. These water-soluble, menthol-soluble polymers act as a binder to provide sufficient adhesion to enable the device to maintain its structural shape. Preferably, the water-soluble, menthol-soluble polymer is carbomer, hydroxypropyl methylcellulose, methyl-cellulose, polyethylene glycol, polyacrylamide, polyvinyl alcohol, poly(N-vinylpyrrolidone), propylene glycol. It is especially preferred that hydroxypropyl cellulose, poly(N-vinylpyrrolidone) or carbomer be used.

In the method of producing the shaped devices of this invention, any substantially water-soluble solid can be employed as a secondary strengthening substance in the device. These secondary strengthening substances need not be menthol-soluble. Exemplary water-soluble solids, in addition to the above polymers include, but are not limited to, vitamins such as ascorbic acid; amino acids such as glycine, arginine and phenylalanine; monosaccharides such as glucose and fructose; disaccharides such as maltose and lactose; polyhydroxy alcohols such as mannitol and xylitol; carboxylic acids such as phenylacetic acid, L-glutamic acid, adipic acid, L-tartaric acid, citric acid and succinic acid; derivatives of carboxylic acids such as urea (an amide); salts of carboxylic acids such as tartrazine (FD&C yellow #5) and sodium citrate; amines such as glutamine; alcohols such as cinnamyl alcohol; and inorganic salts such as potassium chloride, sodium chloride and monosodium glutamate.

Generally, the water-soluble, menthol-soluble polymer comprises about 1% to about 10% of the predevice formulation composition. These quantities provide the finished device with sufficient strength and a satisfactory dissolution rate. It is preferred that about 2% to about 4% of the predevice formulation be water-soluble, menthol-soluble polymer, and especially preferred that about 2% to about 3% of the predevice formulation be water-soluble menthol-soluble polymer. These above percentages correspond to about 5% to about 95% (preferably about 5% to about 30%) of the weight of the actual device (i.e. after sublimation).

The devices of this invention comprise, in addition to the water-soluble, menthol-soluble polymer, one or more beneficial agents. The term "beneficial agents" as used in this specification and the accompanying claims includes, by way of example and not of limitation, any physiologically or pharmacologically active substance that produces a localized or systemic effect in animals. The term "animals" is meant to include mammals including human beings as well as other animals. The physiologically or pharmacologically active substances of this invention need not be soluble in water or in menthol.

Examples of active substances employed in the devices of this invention include, without limitation, inorganic and organic compounds, such as drugs that act on the peripheral nerves, adrenergic receptors, cholinergic receptors, nervous system, skeletal muscles, cardia-vascular smooth muscles, blood circulatory system, synaptic sites, neuroeffector junctional sites, endocrine and hormone systems, immunological system, reproductive system, autacoid systems, alimentary and excretory systems, and inhibitors of autacoids and histamine systems. Drugs that can be delivered for acting on these systems include anti-depressants, hypnotic, sedatives, psychic energizers, tranquilizers, anti-convulsants, muscle relaxants, antisecretories, anti-parkinson agents, analgesics, anti-inflammatory agents, local anesthetics, muscle contractants, antibiotics, anti-microbials, anthelmintics, anti-malarials, hormonal agents, contraceptives, histamines, antihistamines, adrenergic agents, diuretics, antiscabiosis, anti-pediculars, anti-parasitics, anti-neoplastic agents, hypoglycemics, electrolytes, vitamins, diagnostic agents and cardiovascular drugs. Especially preferred pharmaceutical agents include ascorbic acid, acetamino-phen, acetylsalicylic acid, diphenhydramine, doxylamine succinate, meclizine, pseudoephedrine HCl, azithromycin, erythromycin, sultamicillin tosylate, amoxicillin trihydrate, sulbactam sodium, nifedipine, doxazosin mesylate, amlodipine besylate, glipizide, perbuterol HCl, fluconazole, piroxicam, tenidap, sertraline HCl, cetirizine and denofloxacin. Preferably, the formulation includes a unit dose of the beneficial agents. The amount of the beneficial agent employed is based on the clinically established efficacious dose, which ranges from about 0.01 mg to about 1000 mg. The weight ratio of said active ingredient to the carrier is in the range of 1:1 to 1:2500.

Also included in such beneficial agents are prodrugs of the above-described drugs. Such drugs or prodrugs can be in a variety of forms such as the pharmaceutically acceptable salts thereof, and they need not be water-soluble. It is within the scope of this invention that the devices can contain more than one beneficial agent.

The beneficial agents of this invention also include substances for which it is desirable and/or advantageous to control delivery into an environment of use. Examples of such agents, include, but are not limited to, fertilizers, algacides, reaction catalysts, enzymes, and food or drink additives.

In addition to the above described components, other common pharmaceutical excipients may be used. These excipients need not be soluble in menthol. These excipients are generally known in the art, for example, as described in Remington's Pharmaceutical Sciences, 18th Edition (1990), particularly pages 1633 to 1638, and in the Handbook of Pharmaceutical Excipient by the American Pharmaceutical Association. Exemplary excipient include flavoring agents such as natural and artificial orange flavor, grape flavor, artificial banana flavor, strawberry flavor, cherry flavor, peppermint, fruit punch flavor and bubble gum flavor, sweetening agents such as sucrose, aspartame, and alitame, coloring agents such as FD&C red #3 and #40, FD&C yellow #5 and #6, and FD&C blue #2, lubricating agents such as magnesium stearate, sodium lauryl sulfate, talc, polyethyleneglycols, stearic acid, hydrogenated vegetable oils, corn starch, sodium benzoate and sodium acetate, disintegrants such as corn starch, complex silicates, sodium carboxymethyl starch, microcrystalline cellulose, sodium alginate, alginic acid, cross-linked polyvinylpyrrolidone and carboxymethylcellulose sodium, diluents such as lactose, sucrose, dextrose, mannitol, xylitol, sorbitol, sodium chloride, and dibasic calcium phosphate, suspending agents such as acacia, bentonite, calcium stearate, carbomer, gelatin, guar gum, hydroxypropyl cellulose, methyl cellulose, polyvinyl alcohol, povidone, sodium alginate, tragacanth and xanthan gum, emulsifying agents such sodium lauryl sulfate, polyoxyethylene sorbitan monooleate, sorbitan monolaurate, poloxamers, lecithin, acacia, emulsifying wax, and polyethylene stearate. As is clear from the above, the same excipient may be used for different purposes within the same devices of this invention. For example, mannitol and xylitol can be used as both the diluents and the strengthening substances in the device.

The porous devices of this invention have sufficient porosity to provide the devices with the desired strength and dissolution rate. Preferably, the porosity is from about 80% to about 98%. The term "porosity" as used herein refers to the void spaces created by the removal of menthol from the tablet by sublimation. Since the dimensions of the sublimed tablet are unchanged, "porosity" can be expressed either as the percentage of void spaces by volume in the sublimed tablet, or as the percentage of menthol by weight in the tablet formulation prior to sublimation. Preferably, the porosity is about 90% to about 95%. The devices have an open matrix network. The porous devices have high strength (i.e., low friability) as a result of their interconnected network structure. This structure is expressed as a network of water-soluble carrier material having interstices dispersed throughout. The open matrix network of the carrier material is of generally low density. For example the density may be within the range of 10 to 400 mg/cc, preferably 30 to 150 mg/cc, more preferably 60 to 150 mg/cc. The density of the shaped device may be affected by the amount of pharmaceutical substance, or other chemical, or any other ingredients incorporated into the device, and may be outside the above-mentioned limits for the density of the matrix network. The open matrix network, which is similar in structure to a solid amorphous foam, enables a liquid to enter the product through the interstices and permeate through the interior. Permeation by aqueous media exposes the carrier material of both the interior and exterior of the device to the action of the aqueous media resulting in rapid disintegration of the matrix network. The open matrix structure is of a porous and capillary nature which enhances disintegration of the product as compared with ordinary solid shaped pharmaceutical dosage forms, such as tablets, pills, capsules, suppositories and pessaries. Rapid disintegration results in rapid release of any pharmaceutical substance or other chemical carried by the matrix.

Preferably these devices have an amorphous structure. By "amorphous structure" is meant as described in "Solid-State Chemistry of Drugs" by S. R. Byrn (1982), solids in which the atoms and molecules exist in a nonuniform array. This amorphous structure provides greater porosity and a smoother more eye appealing appearance.

In addition, the devices are shaped (i.e., have a predetermined molded shape) except for the open mold side. By "shaped" is meant that at least part of the surface has a form that would not naturally occur through the mere action of gravity. This molded shape may take any convenient form, and preferably includes molded symbols on the surface. The symbols may include logos, brand names, drug identification, doses, etc.

The devices of this invention may be made by any process that results in the tablets having the desired combination of strength, porosity and disintegration rate. Generally, the devices of this invention are made by mixing the desired formulation at a temperature such that the menthol is substantially molten. The molten menthol facilitates the strengthening of the eventual device since the water-soluble, menthol-soluble polymer in conjunction with the menthol forms a solution vs. a mixture and so a more uniform solid structure. Typically, the temperature is at least about 43° C., and is preferably about 43° C. to about 70° C. The molten formulation is then disposed in a die having the desired shape. For example, the formed molten formulation is then allowed to solidify by reducing the temperature to room temperature. Preferably, the solidification occurs by a rapid quench process in which the formulation is exposed to conditions sufficient to result in an amorphous menthol structure. The amorphous menthol structure results in greater porosity, and a preferable eye-appealing appearance in contrast to a crystal menthol structure. In addition, the solidification of menthol results in a slight shrinkage in volume which facilitates the release of the solid matrix from the mold. Typically the solidification occurs at a temperature less than about 40° C., preferably about 0° C. to about −40° C. for a time of at least 10 seconds, preferably about 20 seconds to about 40 seconds. Clearly there is a time-temperature dependency and those skilled in the art can readily select the appropriate combination.

The menthol is then sublimed from the solidified molded formulation. The sublimation may occur prior to or after removal of the solidified device from the die. Preferably the sublimation occurs at a temperature below the melting point of menthol (i.e. 43° C.) and at a pressure of less than about 4 mm Hg. It is especially preferred that the temperature is about 40° C. to about 43° C. and that the pressure is about 2 mm Hg to about 4 mm Hg. Clearly there is a temperature-pressure dependency and those skilled in the art can readily select the appropriate combination to achieve the desired effect (i.e. sublimation of menthol).

Figure 2:
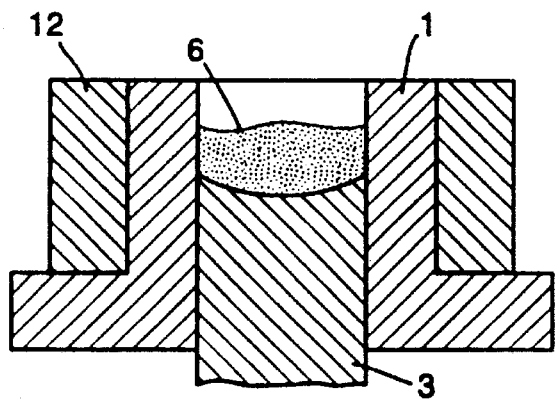
FIG. 2 is a schematic (in cross-section) illustrating the formulation-filled die being solidified.
Figure 3:
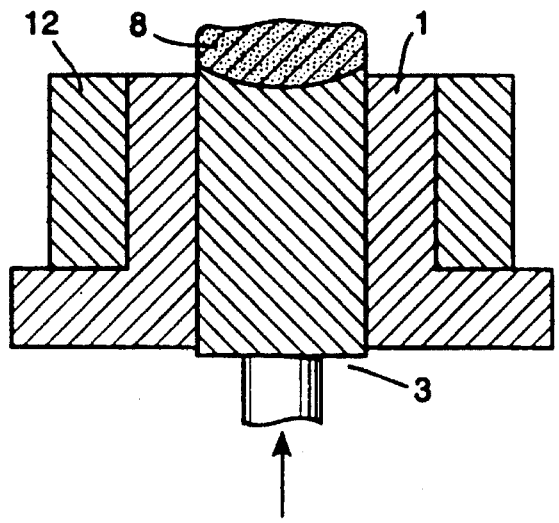
FIG. 3 is a schematic (in cross-section) illustrating the sublimation of the menthol from the solidified shaped formulation.

Referring to the drawings there is illustrated in FIG. 1 a cylindrical die 1. A filling apparatus 4 deposits the molten formulation 6 in the die 1. A refrigeration unit 12 is disposed in contact with the die 1. According to FIG. 2 the desired amount of liquid formulation 6 has been disposed in the cavity formed by the die 1 and punch 3, and is exposed to freezing temperatures by the refrigeration unit 12. According to FIG. 3 the solidified tablet 8 is readily ejected from the die 1 by the action of the bottom punch 3. The solidified device 8 may then be conveniently sublimed (i.e. freezedried). The die and punch assembly can be made of polished tool steel. No lubrication is necessary prior to filling the menthol composition.

The sublimed devices are then available for use as desired. These devices may be used for the oral delivery of pharmaceutical agents to animals, including mammals, particularly, man. These oral delivery devices can be administered as is or dissolved in water prior to administration. In addition, the devices may be utilized for alternative delivery as suppositories, ocular inserts, implants, etc. Finally, these delivery devices may be used to deliver a variety of active ingredients to diverse environments. Exemplary ingredients include fertilizers for agricultural environments, food flavorings for cooking and baking, and sweeteners and cream for coffee and other drinks.

The devices and processes of this invention make a significant advance in the field of delivery devices. The release of the solidified menthol tablet requires no lubrication of the mold as in other processes. The use of menthol in the process provides an efficient process since other systems (e.g. water) can require refrigeration for the removal of water. In addition, due to the high vapor pressure of menthol, the sublimation process for the removal of menthol is much faster than the lyophilization of the same amount of water. Also the solid menthol matrices can be handled at ambient conditions. In addition this method is useful for formulations that are incompatible with water, thus unsuitable for lyophilization. For example drugs that are water-soluble may convert into an unstable form after recrystallization. More commonly, drugs that are taste-masked with a coating may leak out into water if the coating contains water-soluble components.

The devices are highly porous, which facilitates rapid dissolution or disintegration. The rapid dissolution or disintegration facilitates swallowing without water or mastication or both. The rapid dissolution rate also facilitates the use of the device in those instances where such devices are desirable (e.g., veterinary delivery, pediatric patients, geriatric patients). The high strength maintains the device as an integral unit during conventional packaging, transporting and handling, thus assuring the physical integrity of the dosage form, and assuring that the patient receives the proper dosage.

It should be understood that the invention is not limited to the particular embodiments described herein, but that various changes and modification may be made without departing from the spirit and scope of this novel concept as defined by the following claims.

In the following Examples (below), the delivery devices' strength and disintegration rates were determined by a friability test and a disintegration test.

Friability is a measure of tablet strength. The measurement is based on tablet weight loss, expressed as a percentage, after certain numbers of revolutions in the Vanderkamp Friabilator. A low friability value represents better tablet strength.

Disintegration time is measured by the Stoll-Gershberg method using the Erweka tester. The tablet is placed in a perforated basket which is immersed in a 37° C. water bath. During the test, the basket moves in an up-and-down motion. The time needed for complete disintegration of the tablet is recorded as the disintegration time.

The materials used in the following Examples are identified below.

Menthol: USP grade, Spectrum Chemical MFG, Corp.

Klucel EF: hydroxypropylcellulose; Aqualon Company

PEG 3350: polyethylene glycol 3350, Carbowax, Union Carbide

Aspartame: Nutrasweet: Nutrasweet Company

Orange flavor: natural and artificial orange flavor; Firmenich Inc.

Piroxicam: anti-inflammatory agent; Pfizer Inc

Fluconazole: anti-fungal agent; Pfizer Inc

EXAMPLE 1

The following ingredients were blended and milled in a mortar to give a homogeneous mixture. The mixture was then heated on a hot plate to melt the menthol. The molten suspension with the hydroxypropyl cellulose (Klucel-EF) dissolved in menthol was heated to 66° C. with stirring for 30 minutes. Each 1,000 mg suspension contained the following:

| Tablet A Ingredients | Mg/tablet |
| --- | --- |
| Menthol | (900) later removed |
| Klucel-EF | 30 |
| PEG 3350 | 30 |
| Aspartame | 10 |
| Orange flavor | 10 |
| Piroxicam | 20 |
| Total | (1,000) 100 |

A die-and-punch assembly was precooled in a dry-ice container (−78° C.). The 1,000 mg molten suspension was charged into the tableting die with the bottom punch in place. Once frozen, the solid tablet (frozen suspension) was removed from the die. The solid tablet was heated at 43° C. under vacuum in a sublimator for 18 hours to remove the menthol. The final tablet was 90% porous.

Friability after 100 revolutions: 0.0%

Disintegration time: 18 seconds.

EXAMPLE 2

The following ingredients were employed following the same procedure as in Example 1 to prepare 89% porous tablets.

| Tablet A Ingredients | Mg/tablet |
| --- | --- |
| Menthol | (900) later removed |
| Klucel-EF | 30 |
| PEG 3350 | 10 |
| Aspartame | 10 |
| Orange flavor | 10 |
| Fluconazole | 50 |
| Total | (1,010) 110 |

Friability after 100 revolutions: 0.0%

Disintegration time: 20 seconds.

I claim:

1. A method for making a porous delivery device comprising:

a) mixing a formulation comprising menthol, a water-soluble, menthol-soluble polymer, and an active agent at a temperature such that the menthol is substantially molten;

b) disposing said formulation in a mold;

c) solidifying said molded formulation; and d) subliming said menthol from said solidified molded formulation.

2. The method as recited in claim 1 wherein said solidification occurs by exposing said molded formulation to conditions sufficient to provide an amorphous menthol structure.

3. The method as recited in claim 1 wherein said formulation comprises about 80% to about 95% menthol and about 1% to about 10% water-soluble, menthol-soluble polymer.

4. The method as recited in claim 2 wherein said molten formulation is at a temperature at least about 43° C.; said solidification occurs at a temperature less than about 40° C. for a time of at least 10 seconds; and said sublimation occurs at a temperature below 43° C. at a pressure of less than 4 mm Hg.

5. The method as recited in claim 3 wherein the water-soluble, menthol-soluble polymer is hydroxypropyl cellulose or poly(N-vinylpyrrolidone).

6. The method as recited in claim 4 wherein the active agent is a pharmaceutical agent.

7. The method as recited in claim 5 wherein the water-soluble, method-soluble polymer is hydroxypropyl cellulose.

8. The method as recited in claim 6 wherein the pharmaceutical agent is piroxicam or fluconazole.

9. A porous delivery device made according to the method of claim 1.

* * * * *

UNITED STATES PATENT AND TRADEMARK OFFICE
CERTIFICATE OF CORRECTION

PATENT NO. : 5,529,789
DATED : June 25, 1996
INVENTOR(S) : Julian B. Lo

It is certified that error appears in the above-indentified patent and that said Letters Patent is hereby corrected as shown below:

Column 10, line 7 method should be menthol

Signed and Sealed this

Thirteenth Day of May, 1997

Attest:

BRUCE LEHMAN

Attesting Officer

Commissioner of Patents and Trademarks